(12) United States Patent
Farina et al.

(10) Patent No.: US 7,641,855 B2
(45) Date of Patent: Jan. 5, 2010

(54) SYSTEM FOR AUTOMATICALLY STORING AND REPROCESSING PATIENT SAMPLES IN AN AUTOMATIC CLINICAL ANALYZER

(75) Inventors: Edward Francis Farina, Lincoln University, PA (US); Russell John Butler, Berwyn, PA (US); Samuel Garfield Ferguson, Jr., Bear, DE (US)

(73) Assignee: Siemens Healthcare Diagnostics Inc., Deerfield, IL (US)

( * ) Notice: Subject to any disclaimer, the term of this patent is extended or adjusted under 35 U.S.C. 154(b) by 0 days.

(21) Appl. No.: 11/510,173

(22) Filed: Aug. 25, 2006

(65) Prior Publication Data

US 2008/0050278 A1    Feb. 28, 2008

(51) Int. Cl.
G01N 35/02 (2006.01)
G01N 35/04 (2006.01)
G01N 35/10 (2006.01)

(52) U.S. Cl. .................... 422/64; 422/63; 422/65; 436/43; 436/47; 436/48

(58) Field of Classification Search ............ 422/63, 422/64, 65; 436/43, 47, 48
See application file for complete search history.

(56) References Cited

U.S. PATENT DOCUMENTS

| | | | |
|---|---|---|---|
| 5,233,844 A | 8/1993 | Knippscheer et al. | |
| 5,350,564 A | 9/1994 | Mazza et al. | |
| 5,638,686 A | 6/1997 | Coelho et al. | |
| 5,762,872 A | 6/1998 | Buhler et al. | |
| 5,921,102 A | 7/1999 | Vago | |
| 5,964,095 A | 10/1999 | Coelho et al. | |
| 6,068,437 A | 5/2000 | Boje et al. | |
| 6,151,535 A | 11/2000 | Ehlers | |
| 6,649,128 B1 * | 11/2003 | Meyer et al. | 422/63 |
| 6,752,967 B2 * | 6/2004 | Farina et al. | 422/102 |
| 6,793,888 B2 | 9/2004 | Qureshi et al. | |
| 2002/0155590 A1 * | 10/2002 | Gebrian et al. | 435/287.3 |
| 2005/0013736 A1 | 1/2005 | McKeever | |
| 2006/0008384 A1 | 1/2006 | Devlin et al. | |

* cited by examiner

*Primary Examiner*—P. Kathryn Wright
(74) *Attorney, Agent, or Firm*—Leland K. Jordan (57) ABSTRACT

A system for automatically testing a sample aliquot retained in temporary storage in environmentally controlled conditions on an automated clinical analyzer for a period of time without requiring operator intervention.

9 Claims, 9 Drawing Sheets

SYSTEM FOR AUTOMATICALLY STORING AND REPROCESSING PATIENT SAMPLES IN AN AUTOMATIC CLINICAL ANALYZER

FIELD OF THE INVENTION

The present invention relates to an automated clinical analyzer for processing liquid samples, particularly for processing biological fluids such as urine, blood serum, plasma, cerebrospinal fluid and the like. In particular, the present invention provides a method and apparatus to automatically re-test or additionally test an original patent sample stored within a controlled environment in an automated clinical analyzer without operator involvement.

BACKGROUND OF THE INVENTION

Fully automated diagnostic analyzers are commercially available to perform chemical, and immunoassaying of biological fluids such as urine, blood serum, plasma, cerebrospinal fluid and the like. Generally, reactions between an analyte to be measured and reagents used during the assay result in generating some sort of signal that can be measured by the instrument, and from this signal the concentration of analyte in the patient sample may be calculated. Diagnostic analyzers generally employ a large number of various processing stations, where operations such as sample and reagent addition, mix, wash and separate, are performed. Within such analyzers, significant efforts are undertaken to insure that the accuracy of results obtained using automated clinical analyzers is not adversely affected by the various reagents and sample analysis procedures employed in performing different assay process steps, measuring techniques in particular. It is known that much effort has been given to the automated processing of complex immunoassays, including the challenges of maintaining high throughput and analytical accuracy. However, what has been overlooked in the prior art is that regardless of the emphasis placed on the accuracy, precision and throughput of immunoassays, some of the largest potential sources of error concern sample collection, handling methods and even the way the patient is handled before the sample is taken.

For example, if a patient's transferrin level is measured before surgery and after surgery, changes in levels can occur simply as a result of postsurgical stress and such changes might lead to erroneous conclusions that would not have been reached if an original sample had been available for retesting. In this instance, transferrin can fall after about 3 hours and ferritin starts to rise shortly afterwards. Thyroid hormone levels are also often repressed after surgery.

The dietary state of an individual may also lead to conclusions that would not have been reached if an original sample had been available for retesting. It is known that lipid levels change after a fatty meal; liver enzymes are affected by alcohol intake; the renin-aldosterone-angiotensin system is strongly affected by posture; and oral contraceptives have a pronounced effect on many binding proteins including those for thyroxine and cortisol.

Errors in interpretation of immunoassay results may also occur if a second patient sample is not collected correctly. A sample taken from the side on which a mastectomy has been recently done may not be as equally representative of a patient's health condition because of lymphostasis. In other instances, if a second patient sample is taken by needle and a primary sample tube used having a rubber stopper made of a plastic such as tris (2 butoxy-ethyl), the stopper itself may cause displacement of some drugs and other analytes from protein binding sites with consequent redistribution between erythrocytes and plasma. Furthermore, the vagaries involved in urine sample collection are well known.

In such instances, some of the largest potential sources of error concern specimen collection, handling methods and even the way the patient is handled before the specimen is taken. In addition, it may be desirable to repeat the same assay or to conduct other assays on a previously tested sample. For example, if the results of a previously performed assay fall materially outside the range of "expected" test results determined for a number of "normal" patient samples, it may be desirable to repeat the assay a second time for confirmation. For these reasons, original patient samples are often stored in a controlled environment for a period of time after an aliquot portion of the sample is analyzed.

In addition, assay results can serve as the basis for suggesting or requiring additional test assays on an aliquot of a previously tested sample, called reflex or spawned testing. Such reflex tests may be identified by algorithms which specify selection of subsequent assays based on results of previous assays, which concomitantly eliminates the need for human decision-making in selecting the tests, and minimizes the number of necessary tests that have to be run, thus leading to faster and more reliable diagnosis. Such features are tantamount to diagnostic efficiency and cost effectiveness and are popularly employed in clinical chemistry. It is therefore important that the very same patient sample be evaluated as opposed to an additional sample being re-taken for a patient, leading to another necessity to store an original patient sample.

Many commercially available systems for automated storage and retrieval of patient samples are based on Total Laboratory Automation (TLA). TLA systems typically utilize a conveyor system to transport the primary sample tube around the lab from instrument to instrument and then stores the tube in a huge refrigerator for future access. This concept is expensive, involves operator intervention and requires a significant amount of floor space to achieve.

A Storage Retrieval and Disposal System called SRS, produced by CRS Robotics Corporation, is a large stand-alone, automated system that archives primary sample tubes and retrieves them on request. An operator is required to take the sample to the analytical instrument and schedule the add-on tests. U.S. Pat. No. 6,068,437 is typical of such systems and discloses a storage area containing a plurality of racks for storing sample containers, the racks movable throughout the storage area to permit access to all of the racks from an opening in the upper end of the storage area. A robotic transfer apparatus is operable to insert and retrieve sample containers from selected racks in the storage area and move them between the storage area and a buffer area on the housing, as well as between the buffer area and a conveyor located adjacent the housing. The conveyor is of a type which transports sample carriers having a sample container therein, and the buffer area includes a rack for intermediate storage of sample containers.

Alternately, the patient sample may be stored on the analyzer itself in order to avoid the expense of such storage systems as well as to expedite the availability of a sample. The extensive efforts made to achieve these objectives are made clear by an examination of various aspects of modern analyzers.

U.S. Pat. No. 6,793,888 discloses a sample aliquot storage wheel with a pick-and-place mechanism for providing empty vessels and a sample pipettor for aspirating samples from sample tubes and aliquoting samples to empty vessels on the storage wheel. The sample aliquot storage unit has a chiller for controlling the storage environment on said sample storage wheel and means for driving the wheel to position sample vessels for access by the aliquoting station and transporting sample vessels containing sample aliquots back to the storage wheel.

U.S. Pat. No. 5,964,095 discloses a storage container holding an annular rack sealed by an enclosure. The enclosure includes an outer stationary toroid and a rotatable core. A robotic arm is adapted to move and is supported by the core. The robotic arm accesses an interior of the enclosure. An access portal allows removal and placement of thermolabile products constrained by a holder. The robotic arm accesses product and holder and embarks upon controlled freezing of the product and its location in the rack until subsequent retrieval. A computer stores in memory the location of all of the stored products. The robotic arm reads the product in storage to assure the correct product is being accessed.

U.S. Pat. No. 5,921,102 discloses a storage chamber with a carrier disposed inside the chamber for supporting a plurality of samples in a predetermined array, and an access port on the housing for enabling access to the chamber for insertion and retrieval of samples from the carrier. The access port includes an opening in the housing and a drive moves the carrier to juxtapose different samples to the access port. An insertion and removal mechanism alternately inserts and removes samples from the chamber via the access port during operation.

U.S. Pat. No. 5,233,844 discloses a storage chamber and a plurality of sample carriers in the form of annular shelves with pie-slice-shaped openings and disposed one below the other inside the chamber. A rotary drive is operatively connected to the carriers for rotating the carriers independently about a vertical axis. During operation, all openings of all the shelves (except a target shelf) are aligned vertically with an access opening and an insertion and removal mechanism serves to alternately insert and remove samples from the chamber via the opening. Such a system suffers from the disadvantage that all shelves must be rotated into alignment each time a different sample is desired to be extracted.

While these prior art sample storage and retrieval systems have a common objective, none provide the desirable advantage of enabling efficient, random-access to stored samples in combination with directly supplying of stored samples to an analyzer for re-testing.

SUMMARY OF THE INVENTION

In addition to ensuring that the same patient sample is tested a second time following a previous first testing, the apparatus of this invention enabling efficient, random-access to stored samples in combination with directly supplying of stored samples to an analyzer for re-testing or additional testing without the necessity for operator intervention. This invention provides a system for automatically reprocessing a second test sample of a sample aliquot retained in temporary storage in environmentally controlled conditions on an automated clinical analyzer. The analyzer is computer-controlled and operated and has aliquot arrays positioned in aliquot array test sampling tracks, the arrays containing aliquot sample portions of an original patient sample container. Aliquot array storage racks are provided for storing the aliquot arrays within an environmentally controlled chamber and an elevator-like device places the storage racks into and removes them from the chamber. After storage, the aliquot arrays are replaced onto test sampling tracks, test sample portions are aspirated from a sample aliquot portion within the aliquot array and dispensed for testing.

Incoming samples to be tested are identified, for example by bar coded indicia placed on the original sample container to identify, among other items, the patient's identity. Based on the patient's identity, the computer-controlled analyzer is operated to perform a number of requested assays and to retain an aliquot portion of the original patient sample for designated periods of time after the completion of pre-defined events. Two original aliquot portions of sample may aspirated from the original sample container, and in accord with one embodiment of the present invention, are dispensed into two separate wells in an aliquot array. Test sample fluids, or test samples, are subsequently aspirated from either one or both of the wells and analyzed by the analyzer. After aspiration of the test samples, the aliquot array is retained in a storage compartment within the analyzer under controlled environmental conditions. If it becomes desirable to re-test or additionally test a patient's sample after tests on the first test sample are completed, for example to provide for reflex testing or in the event of repeating a test following an very abnormal analytical result, the aliquot array containing the original aliquot portions of sample is removed from the controlled environmental storage using the random-access environmental storage chamber of the present invention, test samples are aspirated from the appropriate well and are re-tested without operator intervention. In addition to efficiency in re-testing and eliminating operator intervention, the present invention provides for the same original patient sample to be tested to minimize if not totally eliminate the potential sources of error that exist in repeated sample collection.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
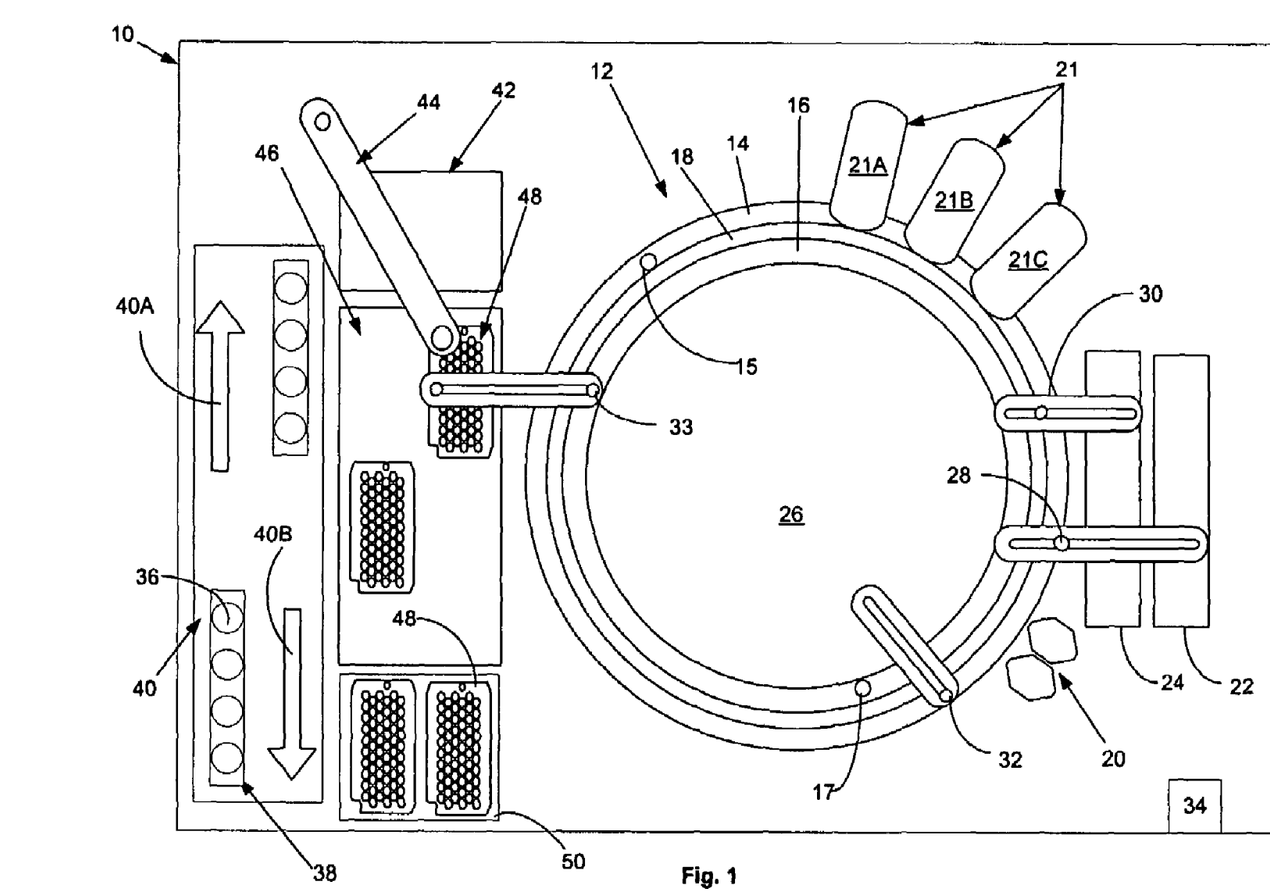
FIG. 1 is a schematic plan view of an automated analyzer in which the present invention my be advantageously employed.

FIG. 1 shows schematically the elements of a conventional automatic chemical analyzer 10 in which the present invention may be advantageously practiced. Analyzer 10 comprises a reaction carousel 12 supporting an outer cuvette circle 14 of cuvette ports 15 and an inner cuvette circle 16 of cuvette ports 17, the outer cuvette circle 14 and inner cuvette circle 16 being separated by a groove 18. Cuvette ports 15 are adapted to receive a plurality of reaction cuvettes typically formed as small, flat walled, U-shaped containers having an open central reaction portion closed at the bottom and with an opening at the top to allow the addition of reagent and sample liquids. Cuvette ports 17 are adapted to receive a plurality of similar reaction cuvettes except being round walled. Reaction carousel 12 is rotatable using stepwise movements in a constant direction at a constant velocity, the stepwise movements being separated by a constant dwell time during which dwell time, carousel 12 is maintained stationary and individual computer controlled electro-mechanical devices 20, such as sensors, reagent add stations, mixing stations, and the like, perform the actions required in well known clinical assays. Such devices and their control and operation are described, for example, in U.S. Pat. Nos. 5,876,668, 5,575,976 and 5,482,861 and the references cited therein.

Three temperature-controlled reagent storage areas 22, 24 and 26 each store a plurality of reagent containers containing reagents as necessary to perform a given assay. Shuttle means (not shown) move individual cartridges to probes 28, 30 and 32, respectively. Storage areas 22 and 24 may be conveniently located external to the circumference of outer cuvette circle 14 and reagent storage area 26 may be conveniently located internal to the circumference of inner cuvette circle 16. Various assay analyzing means 21 may be located proximate outer cuvette carousel 14 and are adapted to measure light absorbance in or emission from cuvettes 15 at various wavelengths, from which the presence of analyte in the sample liquid may be determined using well-known analytical techniques. Means 21 typically comprise conventional photometric 21A, fluorometric 21B or luminescent measuring devices 21C adapted to perform an interrogating measurement at any convenient time interval during which reaction carousel 12 is stationary.

Analyzer 10 is controlled by computer 34 based on software written in a machine language, like that used on the Dimension® clinical chemistry analyzer sold by Dade Behring Inc, of Deerfield, Ill., and widely used by those skilled in the art of computer-based electromechanical control programming. Computer 34 is interlinked using known interface software applications with a Laboratory Information System (LIS) and/or a Hospital Information System (HIS) so that information concerning patients, patient assay requests, assay results, analyzer status, and the like, may be immediately accessible as needed by laboratory personnel. Computer 34 includes an operator interface module typically comprising a keyboard and monitor or a flat-panel touch viewing screen or the like, on which information about the operational status of analyzer 10 as described herein may be called up and displayed or by which analyzer 10 may be automatically controlled to perform assays and related operations given the identity of a patient sample and assay requests, results and desired on-board storage conditions.

In order to clearly describe the method and apparatus exemplary of the present invention for automatically storing and re-testing patient samples in an automatic clinical analyzer, the operation of analyzer 10 while practicing the present invention will be described without providing details of how a number of well known electromechanical operations may be conventionally conducted under the control of a programmed computer 34. Conventional operations such as controlling the movement and placement of sample rack and tubes and aliquot arrays, liquid aspiration and dispensing operations by sampling arms and probes, coordination of alignment and activation of drive, rotation, extracting and lifting motors, the role of proximity and location sensors, bar-code readers in providing operational status data to computer 34 and the like are well known in the art and have been described in readily available publications.

As seen in FIG. 1, incoming sample samples to be tested are typically contained in sample containers or tubes 36 supported in sample tube racks 38 transportable by a sample tube rack transport system 40 comprising incoming lane 40A and outgoing lane 40B. Bar coded indicia on sample tubes 36 are scanned using a conventional bar code reader to determine, optionally among other items, a patient's identity, the tests to be performed, and if a sample aliquot is desired to be retained inside an environmental storage chamber 42, described hereinafter.

Figure 2:
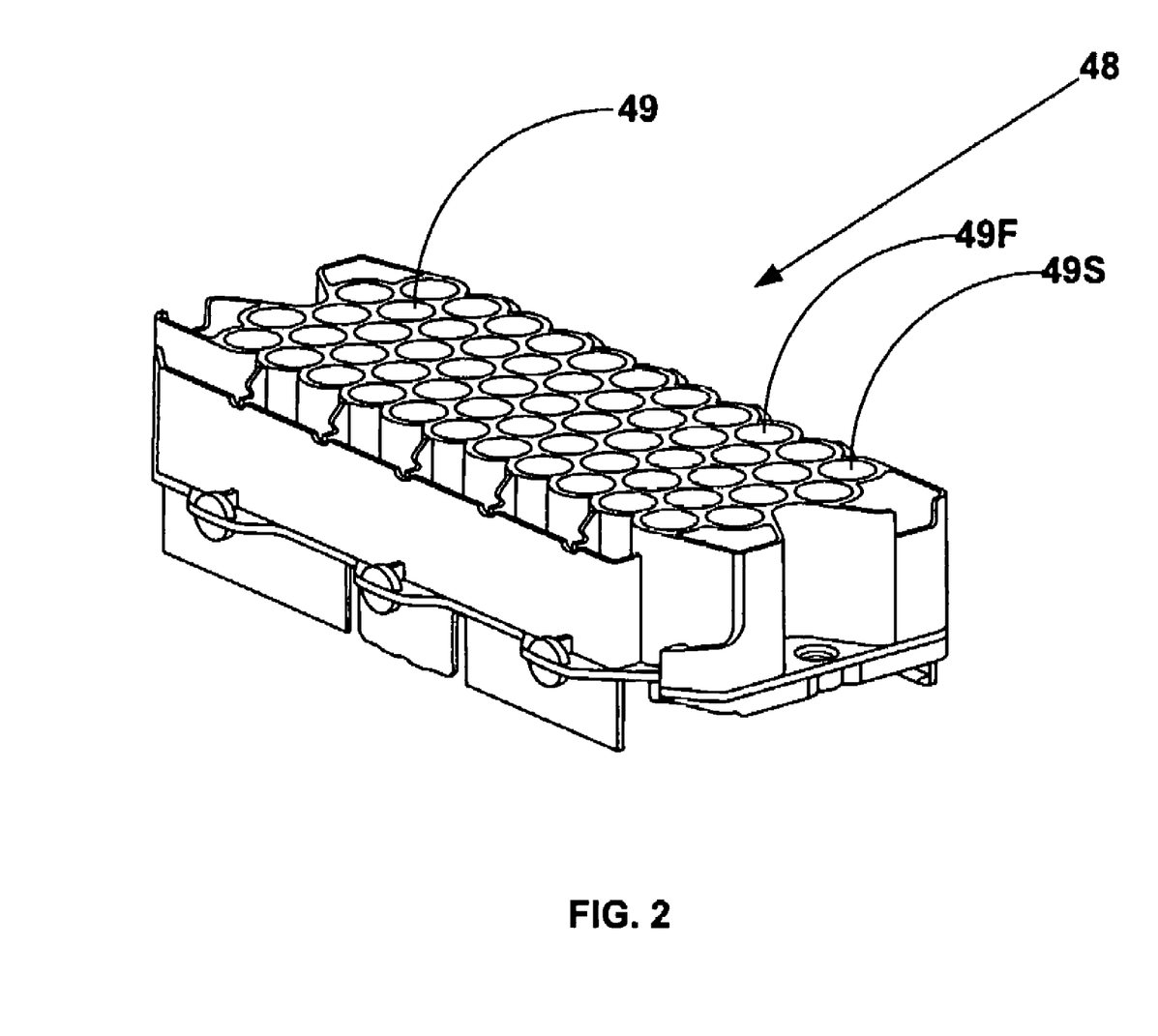
FIG. 2 is an aliquot array useful in the analyzer of FIG. 1.
Figure 3:
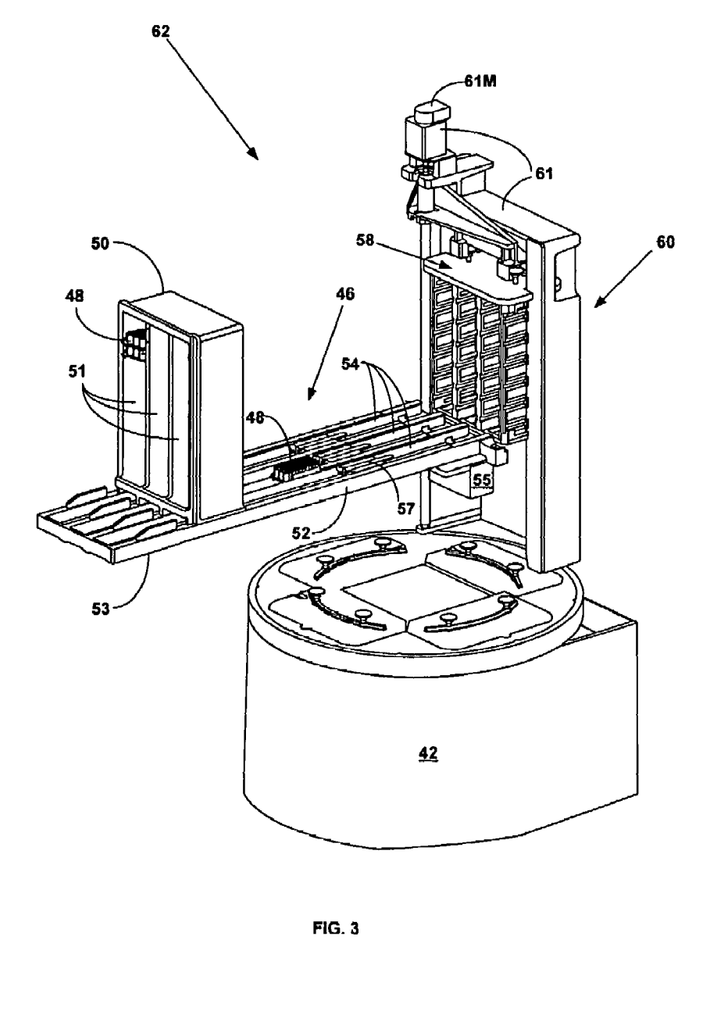
FIG. 3 is a perspective view of an automatic sample storage and re-testing system exemplary of the present invention for automatically storing and re-testing patient samples in an automatic clinical analyzer like see in FIG. 1.

Aliquoting probe 44 supports a conventional liquid aspiration probe and is rotatably mounted so that movement of aliquot probe 44 describes a line intersecting the original patient sample tubes 36 transported by sample tube transport system 40 and an aliquot array transport system 46 seen in FIG. 3. Aliquot array transport system 46 comprises an aliquot array handling unit 50 like that described in U.S. Pat. No. 6,752,967 and adapted so that aliquot arrays 48 like seen in FIG. 2 may be automatically transferred from a vertical stack of aliquot arrays 48 contained within aliquot array inventory shafts 51 onto a planar aliquot array transport system 46 having a number of parallel aliquot array test sampling tracks 54 formed therein. A shuttle mechanism 53 may be employed to facilitate supply of aliquot arrays 48 into test sampling tracks 54. Aliquot array 48 has an ordered array of open wells 49 formed on a base plate and extending upwardly therefrom between the pair of parallel side walls and a zero-backlash hitch in the central region of a front shorter perimeter portion. Each aliquot array 48 is marked, for example with machine-readable indicia so that the identity of the array 48 and thus the identity and location of each patent sample aliquot within each well 49 may be tracked and located using routine computed-aided tracking programs within computer 34. Optionally, array 48 may be covered with a lidstock having I-shaped, X-shaped, or star-shaped slits forming adjacent segments that act to partially seal around an aspiration probe. Bi-directional aliquot array drive motors 55 are positioned beneath array transport system 46 and are controlled by computer 34 to shuttle aliquot arrays 48 lengthwise within test sampling tracks 54, for example by a motor-driven dolly 57 independently moveable in either direction within test sampling tracks 54 to a test sampling location within test sampling tracks 54.

Figure 4:
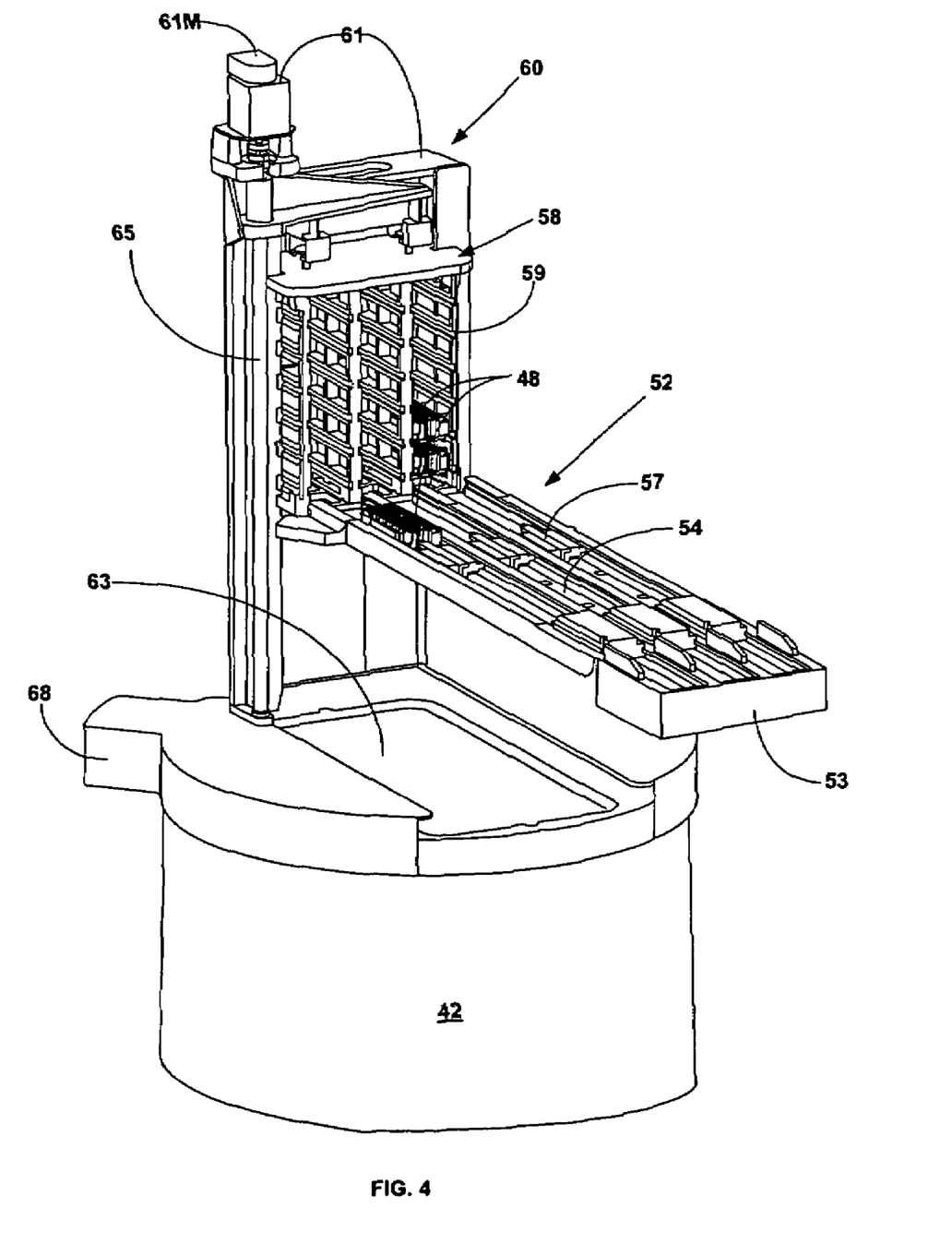
FIG. 4 is a partial perspective view of the apparatus of FIG. 3 illustrating the automatic transfer of aliquot arrays like seen in FIG. 2 via an aliquot array transport member into aliquot array storage racks of the sample storage and re-testing system of FIG. 3.
Figure 5:
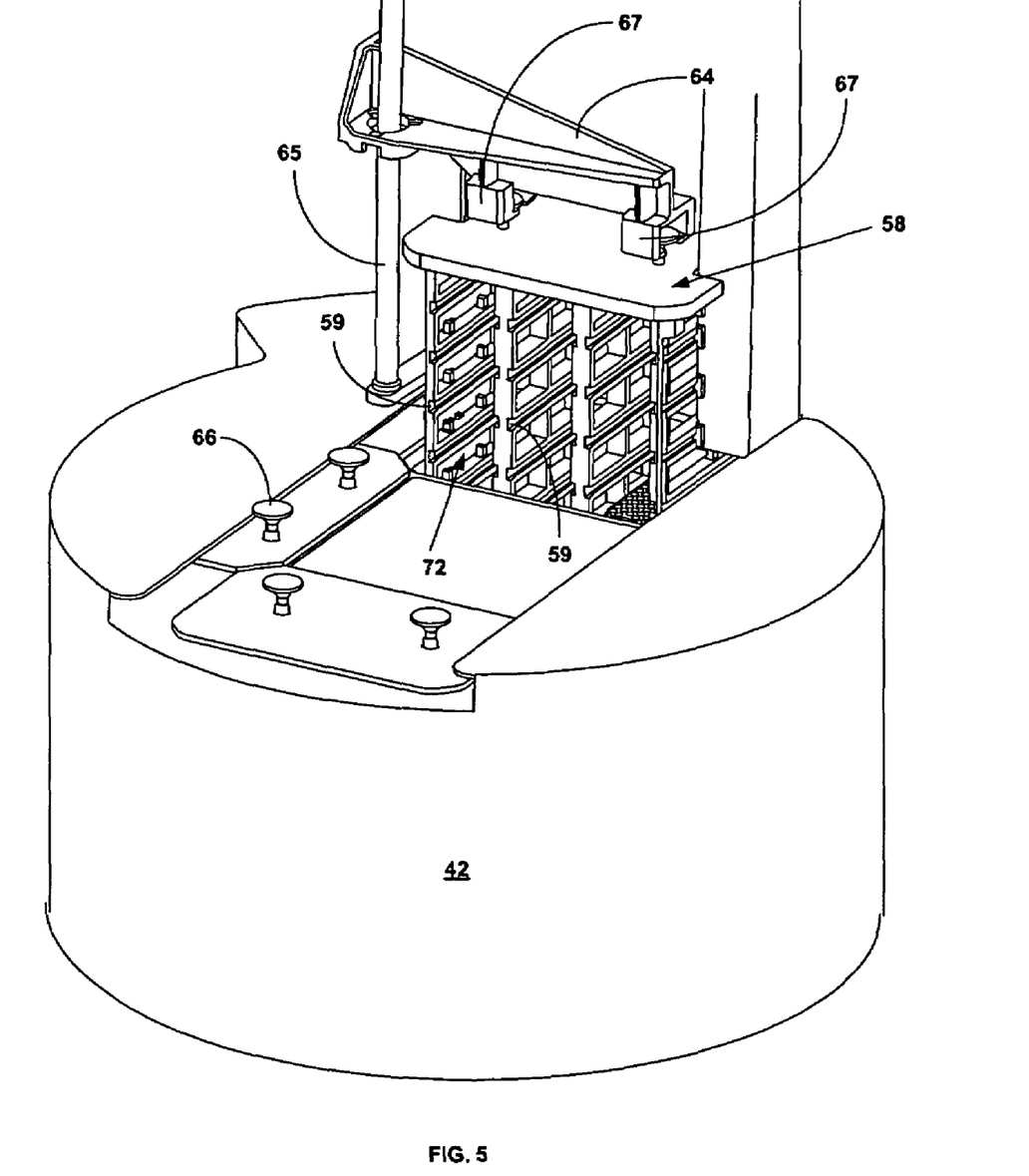
FIG. 5 is a perspective view of the apparatus of FIG. 4 illustrating a sample storage rack partially inserted or removed from a controlled environment chamber.

Aliquot probe 44 is conventionally controlled by computer 34 to aspirate liquid sample from sample tubes 36 and to dispense one or more aliquot portions of the original patient sample into one or more of wells 49 in aliquot arrays 48, depending on the quantity of sample required to perform the requisite assays and to provide for at least one aliquot portion to be retained by analyzer 10 within environmental chamber 42. In an exemplary embodiment, two separate sample aliquot portions are dispensed into two separate wells 49 in an aliquot array 48. Subsequent to dispensing aliquot portions of an original patient sample into wells 49, drive motors 55 are controlled by computer 34 to position aliquot array 48 at a test sampling position within vessel array tracks 54 below a test sample test sampling probe 33 located proximate reaction carousel 12 (FIG. 1). Test sample sampling probe 33 is controlled by computer 34 to aspirate a requisite test sample volume(s) into reaction cuvettes in cuvette ports 15 and 17 in order to perform the original menu of assays prescribed for the sample. After sample has been dispensed into reaction cuvettes, and while the aliquot array 48 is within one of the test sampling tracks 54, an empty slot 59 within an aliquot array storage rack 58 of a storage rack elevator system 60, seen in FIGS. 4 and 7 and described hereinafter, is vertically aligned by a stationary shaft drive motor and frame unit 61 (FIG. 3) with the aliquot array 48 and test sampling tracks 54 and array drive motors 55 are controlled by computer 34 to insert aliquot arrays 48 into a slot 57 for subsequent storage in aliquot array storage system 62 as described hereinafter (FIG. 4).

Figure 6:
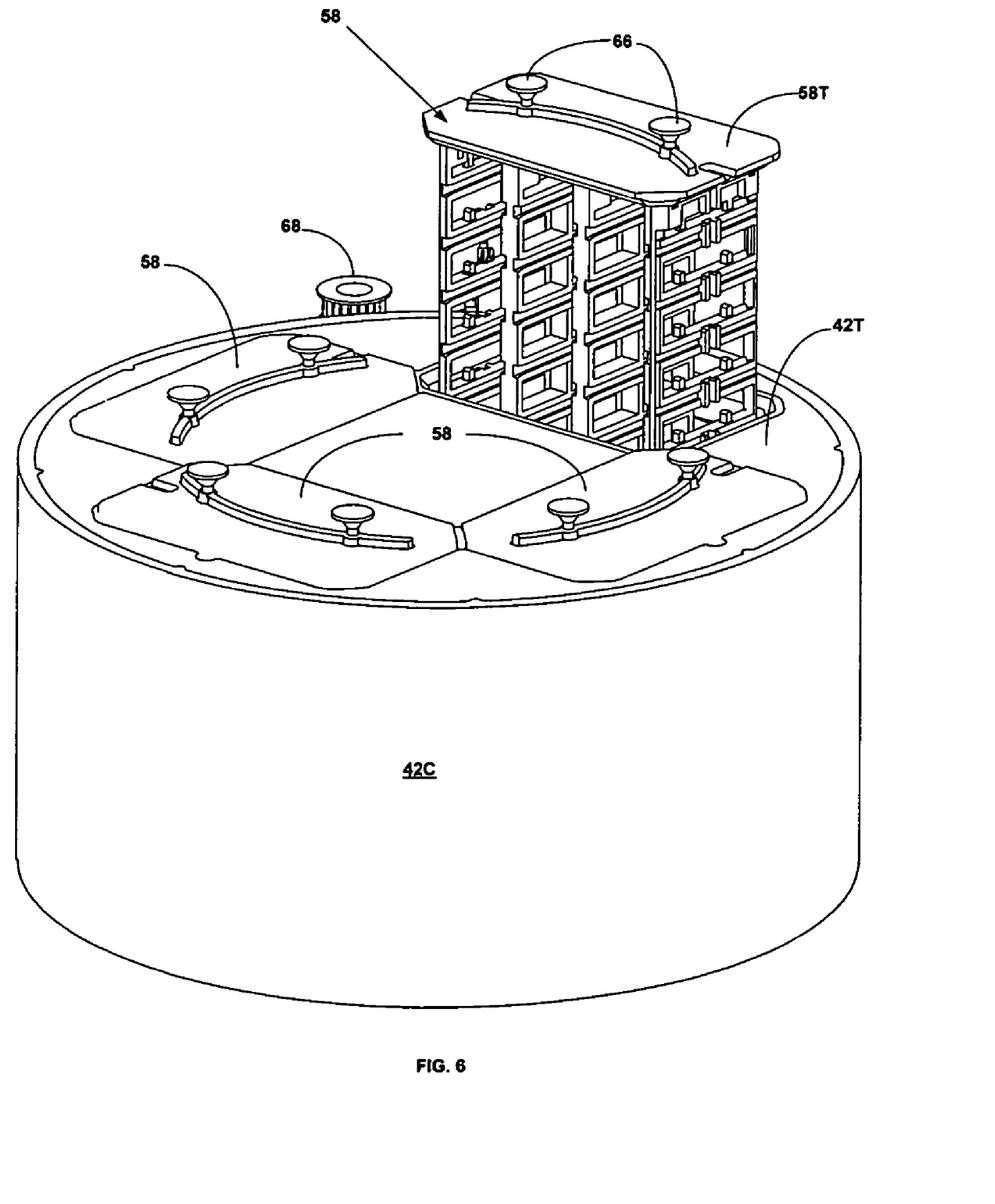
FIG. 6 is a perspective view of the apparatus of FIG. 4 illustrating sample storage racks partially removed and fully contained within the controlled environment chamber of the apparatus of FIG. 4.

Aliquot array storage system 62 is provided as an integral portion of analyzer 10 in order to expedite and facilitate re-testing of patient samples and is operated by computer 34 to ensure that the same patient sample is automatically available for testing a second time following a previous first testing whenever such re-testing is desirable. As seen in FIGS. 4-9, aliquot array storage system 62 of the present invention comprises an environmentally controlled storage compartment 42 having an upper opening 63 through which aliquot array storage racks 58 containing aliquot arrays 48 having aliquot portions of original patient samples in wells 49 may be raised or lowered by elevation means illustrated as a vertically translatable latch arm 64. Storage compartment 42 preferably comprises a rotatable insulated structural foam rack carousel 42C with an insulated top 42T and integral air distribution channels 42A with an opto-interrupter sensor located therein to indicate home position for the carousel 42C as well as identifying the presence of storage racks 58, also having an insulated top plate 58T. A conventional temperature and humidity controlling unit is connected to storage compartment 42 to maintain the internal environment within a temperature range of about $-4°$ C. to $+20°$ C. and within a humidity range of about 80-100% RH, non-condensing. Latch arm 64 is attached to and extends perpendicularly from computer controlled vertical drive means, typically a conventional screw-like drive shaft 65 driven by a shaft drive motor 61M located at the top of shaft drive motor and frame unit 61 attached to an upper, external surface of chamber 42. Storage racks 58 are provided with a pair of knobs 66 (FIG. 6) that may be engaged by a pair of open-ended and open-bottom C-shaped hooks 67 depending from the lower surface of latch arm 64. FIG. 6 shows three storage racks 58 fully disposed within chamber 42 and one storage rack 58 partially removed from chamber 42 at an exemplary location of shaft drive motor and frame unit 61 for illustrative purposes. An important feature of environmental chamber 42 is a chamber stepper motor 68 connected by means of appropriate gearings to rack carousel 42C and controlled by computer 34 to house the four storage racks 58 in a circular pattern within chamber 42. Rack carousel 42C is rotatable, for example by an external belt drive by stepper motor 68 so that that any one of the racks 58 may be located in a vertically aligned position beneath opening 63 and latch arm 64. Knobs 66 are slidable into a locking position within C-shaped hooks 67 as a rack 58 is rotated, thus enabling latch arm 64 to secure a storage rack 58 for removal from environmental chamber 42.

Figure 7:
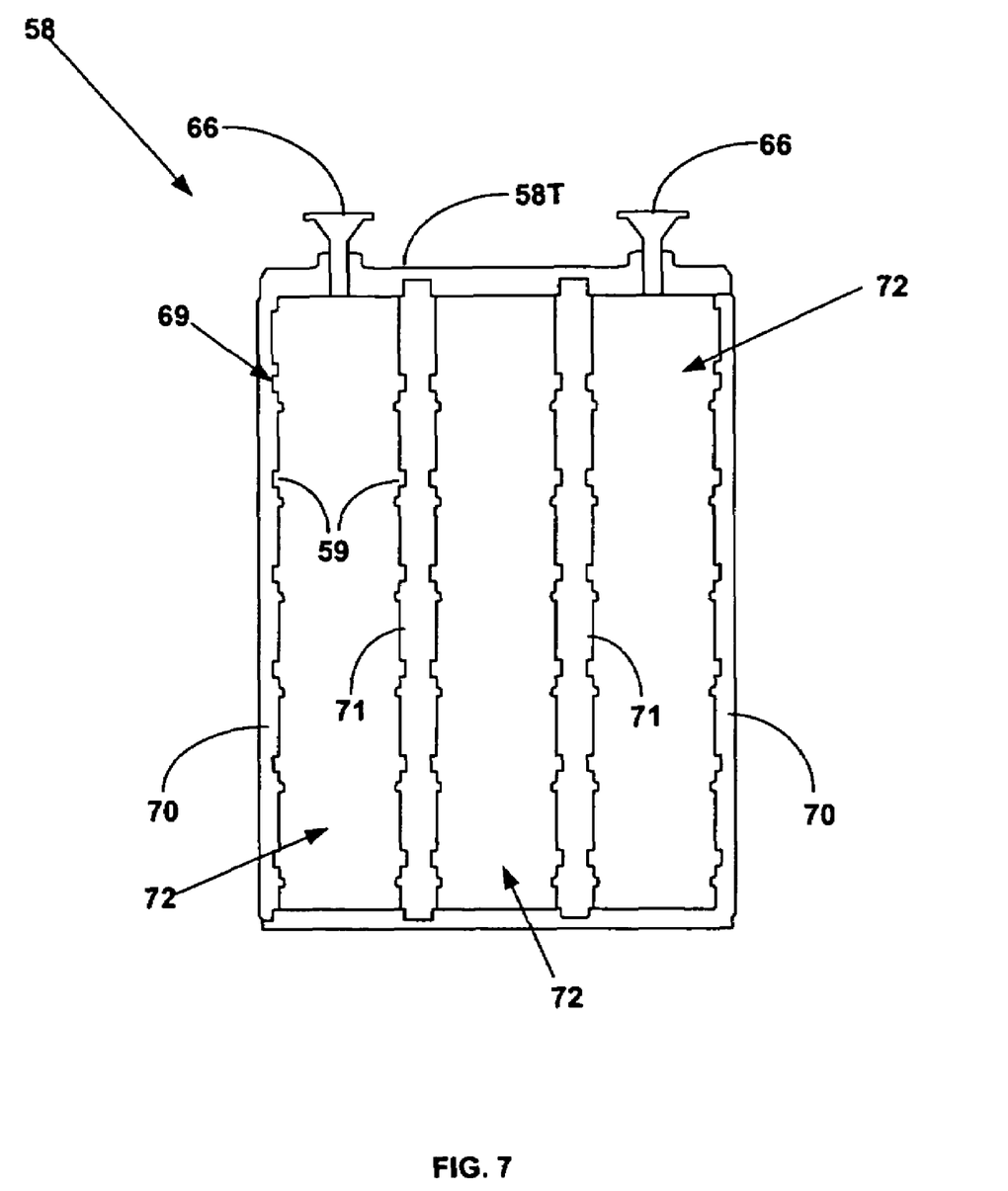
FIG. 7 is a sectional view of the storage racks contained within the controlled environment chamber of the apparatus of FIG. 4.

By means of latch arm 64 attached to shaft 65, shaft drive motor 61 is controlled by computer 34 to vertically remove a storage rack 58 from the interior of carousel 42C to a number of step-wise elevations above chamber 42, each such stepwise elevation corresponding to a height in sequential parallel alignment with vessel array test sampling tracks 54. In accord with the present invention, storage rack 58 may be vertically positioned at a number of locations whereat a corresponding number of aliquot arrays 48 may be singularly inserted by array drive motors 55 of aliquot array transport system 46 operated under the control of computer 34 into a number of confining storage slots 59. Slots 59 are formed by pairs of parallel, horizontally spaced apart tracks 69 formed in the inner surfaces of vertically oriented external storage rack rails 70 and in two opposed internal surfaces of vertically oriented central storage rack rails 71 (FIG. 7). Importantly, as best seen in FIG. 7, a sectional view of a storage rack 58, storage rack 58 comprises two external rails 70 and two internal rails 71 spaced apart to form three aliquot array storage shafts 72 each sized to hold an aliquot array 48 between tracks 59. Importantly also, the aliquot array storage shafts 72 are also spaced apart the same distance as are vessel array test sampling tracks 54 sc that each of the three aliquot array storage shafts 72 can be aligned with a corresponding one of the vessel array test sampling tracks 54 (FIG. 4A). Consequently, aliquot array storage shafts 72 may be operatively connected to aliquot array test sampling tracks 54 of aliquot array transport system 46 by means of array drive motors 55 so that storage rack 58 and sampling tracks 54 are operatively connected to directly insert an aliquot array 48 into a sampling track 54.

Figure 8:
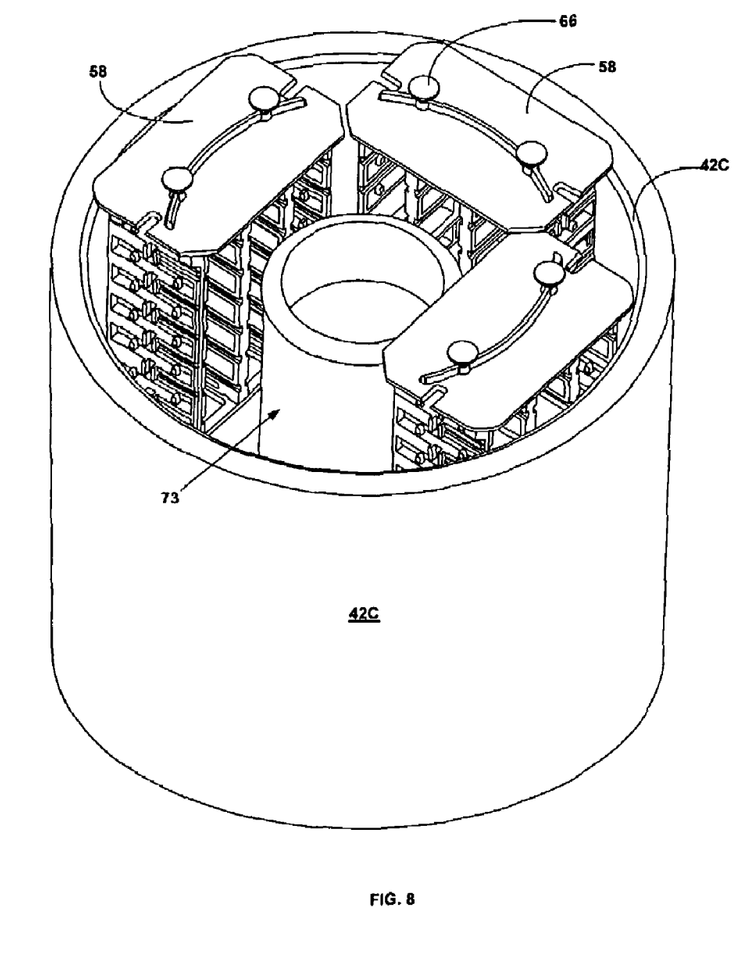
FIG. 8 is a perspective view of the apparatus of FIG. 4 illustrating three sample storage racks stored within a rotatable storage carousel within the controlled environment chamber of the apparatus of FIG. 4; and, FIG. 9 is a sectional view of the rotatable storage carousel of FIG. 8.
Figure 9:
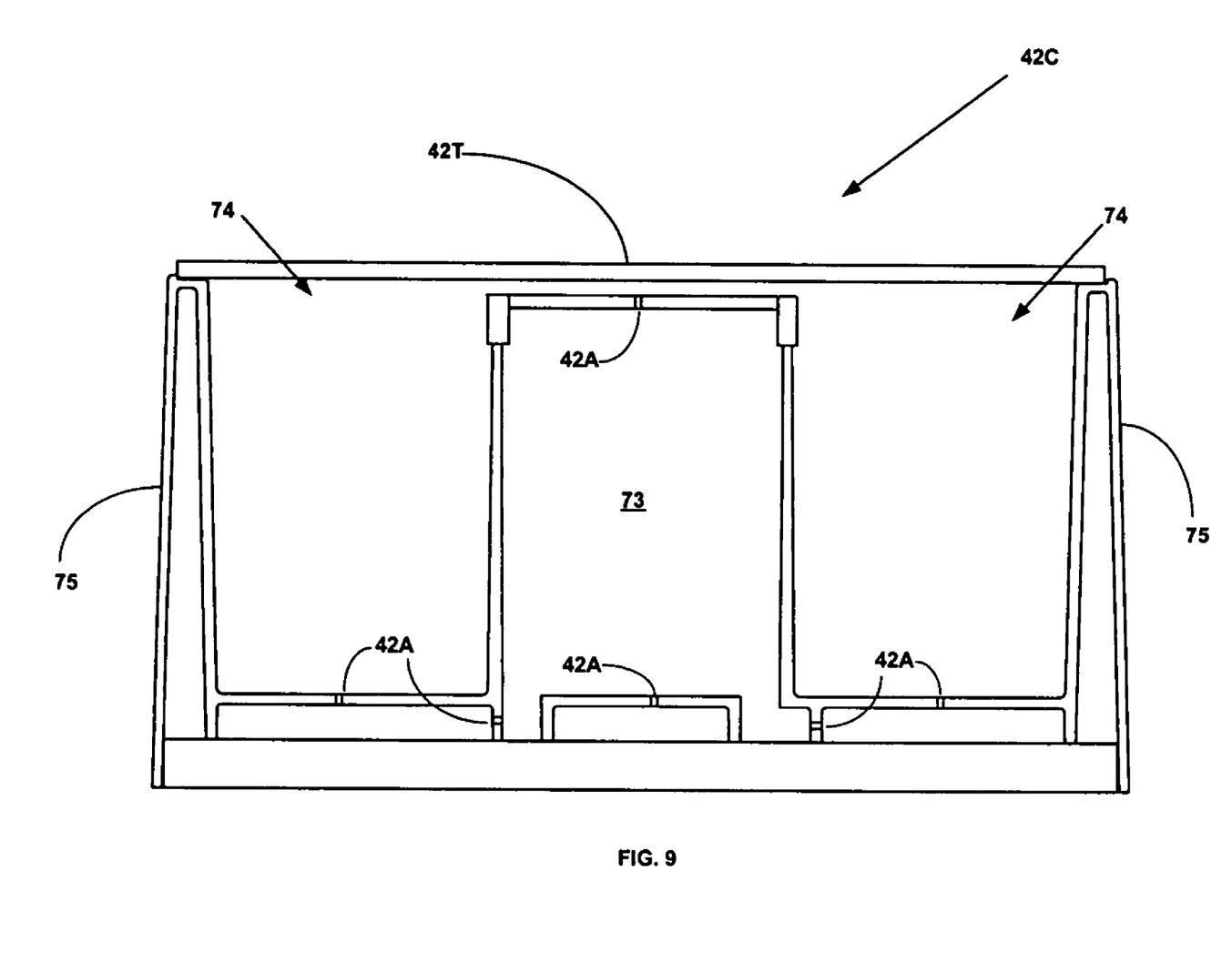

FIG. 8 is a view of three storage racks 58 stored within rotatable carousel 42C which is nested within environmental chamber 42. Carousel 42C is seen to comprise an open central core 73 around which a circular trough 74 is formed within the external wall surface 75 of carousel 42C. FIG. 9 is a sectional view of carousel 58 further illustrating a number of the integral air distribution channels 42A.

In FIG. 3, array transport system 46 is illustrated as suspended for purposes of clarity; however it is to be understood that, as seen in FIG. 1, array transport system 46 is an integral portion of the operating surface of analyzer 10 and is fixed between aliquot array storage and handling unit 50 and storage rack elevator system 60. The above described storage rack 58 positioning feature enables rapid access of latch arm 64 to any one of the storage racks 58 within chamber 42 and, taken in conjunction with the capability of latch arm 64 to vertically position any aliquot array 48 stored within a storage rack 58 in alignment with a corresponding aliquot array test sampling track 54 permits any aliquot array 48 stored on-board analyzer 10 in chamber 42 to be rapid accessed in a random manner and re-placed by within an aliquot array test sampling track 54. Once re-placed onto an aliquot array test sampling track 54, drive motors 55 under the control of computer 34 re-position the aliquot array 48 at a test sampling position within vessel array tracks 54 below test sampling probe 33 proximate reaction carousel 12 whereat a sample of the original patient aliquot sample may be aspirated as required to perform an assay thereon and dispensed as required into a reaction cuvette 19. In addition to ensuring that the same patient sample is tested a second time following a previous first testing, the efficient, random-access accessibility of stored samples by aliquot array storage system 62 of the present invention operated as described above under the control of computer 34 and in conjunction with aliquot array storage and handling unit 50 eliminates the necessity for operator intervention. Removal of storage rack 58 from within environmental chamber 42 is accomplished simply by reversing the process described for placement of an aliquot array 48 into environmental chamber 42.

As described above, the present invention provides analyzer 10 with a system for automatically and quickly re-testing a sample taken from at least one and/or an additional original patient sample aliquot that has been placed into and retained in the environmental chamber 42 of analyzer 10 for a period of time. Incoming samples to be tested are identified by reading with a conventional bar code reader indicia placed on the sample container defining, among other items, a patient's identity, the tests to be performed and if a sample aliquot is desired to be retained. In addition to a first sample aliquot portion taken by aliquoting probe 44 from sample tubes 36 containing the sample to be tested, dispensed into a first well 49F (FIG. 2) of aliquot array 48, and then aspirated and dispensed into a reaction cuvette 15 or 17 by sampling probe 33, a second sample aliquot portion may also be aspirated by aliquoting probe 44 from the sample and this second sample aliquot may be retained by analyzer 10 within a second well 49S of aliquot array 48 within environmental chamber 42 for sampling by sampling probe 33 and re-testing on analyzer 10. An important feature of the present invention is the availability of first and second aliquot sample portions stored in first and second wells 49F and 49S, the first portion being sampled by sampling probe 33 to provide samples for tests having a normal level of assay sensitivity and thus requiring a standard degree of aspiration probe cleansing; in contrast, the second portion is sampled by sampling probe 33 to provide samples for tests having a higher level of assay sensitivity and thus requiring a higher level of aspiration probe cleansing. Because increasing the level of probe cleansing requires additional time and cleaning resources, having two separate original sample aliquot portions available for re-testing, analyzer throughput may be increased by test sampling from the first aliquot portion for tests having a normal level of assay sensitivity.

In one embodiment, two sample aliquot portions are retained within environmental chamber 42 for every original patient sample presented to analyzer 10 for a period of time after tests on the sample taken from a aliquot portion by test sampling probe 33 are completed. In this instance, the period of time that the sample aliquot portion is retained for additional or re-testing depends upon the assay volume demand placed on the analyzer because sample aliquot portions would be placed into a storage rack 58 and removed therefrom and disposed of on a first-in-first-out basis. In an exemplary embodiment, there are 57 wells 49 on each aliquot array 48, and four storage racks 58 each retaining 18 arrays 48. If two aliquot portions are stored in separate wells 49, a total of about 2000 original patient sample may be stored by analyzer 10. Analyzer 10 may be a high volume analyzer capable of about 6,000 assays per day, and at an average of six assays per patient sample, aliquot portions would be retained on analyzer 10 for about two days. At any time during the period of time the aliquot portion is retained on analyzer 10 and a request is made to repeat a test or to perform additional tests on the previously tested patient sample, this request is presented to analyzer 10 either by an operator or automatically by a Laboratory Information System (LIS) electronically connected to analyzer 10. Either the LIS or the operating computer 34 is provided with assay-specific information identifying the maximum amount of storage time an assay may be safely conducted after aliquot portions of the original patient sample are aliquoted by probe 44. If the aliquot portion has been retained within storage carousel 420 for less than that safe maximum amount of storage time, the operating computer 34 of analyzer 10 subsequently provides appropriate electro-mechanical machine instructions to rack carousel stepper motor 68 to rotate the storage rack 58 within rotatable carousel 42C having the appropriate aliquot array 48 containing the containing the second aliquot of the previously tested patient sample to a location beneath opening 63. As described above, knobs 66 on storage rack 58 are slidable into a locking position within C-shaped hooks 67 as rack 58 is so rotated enabling latch arm 64 to secure a storage rack 58 for removal from environmental chamber 42C. Computer 34 then operates shaft drive motor 61M to lift storage rack 58 to the height at which the aliquot array 48 containing the second aliquot of the original patient sample is in vertical alignment with one of the vessel array test sampling tracks 54. Computer 34 then operates array drive motors 55 to remove the aliquot array 48 from a storage slots 59 and to insert the aliquot array 48 into aliquot array test sampling tracks 54 of aliquot array transport system 46. Once inserted into an aliquot array test sampling track 54, drive motors 55 under the control of computer 34 re-position the aliquot array 48 to present the second aliquot of the previously tested original patient sample to test sampling probe 33 where a portion or all of the second sample aliquot is aspirated by test sampling probe 33 and dispensed into a reaction cuvettes 15 or 17 as required to complete the requested tests on the previously tested patient sample. Operation of analyzer 10 then proceeds to complete the tests requested on the second sample aliquot of the previously tested patient sample, without requiring that a second patient sample be obtained. In contrast, If the aliquot portion has been retained within storage carousel 42C for an amount of time greater than that safe maximum amount of storage time for the assays requested to be conducted, the operating computer 34 of analyzer 10 will provide an alert signal and the assay will not be conducted until a new original patient sample is made available.

In an alternate embodiment, a second sample aliquot may be taken by aliquoting probe 44 only from those sample tubes 36 that have bar code indicia related to instructions to retain such a second sample aliquot on-board analyzer 10. In this instance, the bar code indicia may also containing instructions that establish the particular period of time that the second sample aliquot is retained in an aliquot array 48 within environmental chamber 42 after tests on the corresponding first sample aliquot are completed. Obviously, in this second embodiment, the bar code indicia may simply instruct that the second sample aliquot be retained within environmental chamber 42 for some standard period of time. Similarly to the previous embodiment, at any time during the period of time that the second sample aliquot is retained within environmental chamber 42C, a request to repeat a test or to perform additional tests on the previously tested patient sample, may be automatically performed by analyzer 10, without requiring that a second original patient sample be obtained, if the aliquot portion has been retained within storage carousel 42C for less than the corresponding assay-specific safe maximum amount of storage time.

In another embodiment, a second sample aliquot may be taken by aliquoting probe 44 only from those sample tubes 36 that have bar code indicia containing instructions for analyzer 10 to perform certain analytical tests or groups of tests and the bar code indicia do not contain instructions either to store or regarding a specific time to store such a second sample aliquot on-board analyzer 10. In this embodiment, computer 34 contains a look-up-table in memory that automatically establishes from the analytical tests or groups of tests requested whether or not a second sample aliquot should be retained in an aliquot array 48 within environmental chamber 42. For example, if a Standard Metabolic Panel (CHEM 8) including Na, K, Cl, CO2, GLUC, BUN, CREA, and CA is to be performed, the second sample aliquot may be automatically retained in an aliquot array 48 for the established period of time.

In another instance, if the original patient sample is to be tested for indications of abnormal levels of drugs of abuse or prostrate specific antigen, tests that may be done as part of a routine employment examination or to diagnose a highly specific disease, the period of time that the second sample aliquot is retained in environmental chamber 42 may be as short as one day, since no additional or repeated testing is expected. In contradistinction, if the original patient sample is to be tested for indications of abnormal PSA levels, a test that is not done as part of a routine examination, the period of time that the second sample aliquot is retained in environmental chamber 42 may be as long as it may be safely stored within storage carousel 42C, since additional or repeated testing may be expected as part of a full diagnosis. Obviously, in such an instance, the aforementioned first-in-first-out protocol for managing aliquot samples may be over-ridden by computer 34 to allow for exceptional storage requirements.

In an even further embodiment, a second sample aliquot is taken by aliquoting probe 44 from every patient sample and is retained in an aliquot array 48 within environmental chamber 42 for a relatively short period of time after tests on the corresponding first sample aliquot are completed. In this embodiment, the purpose of storing a second sample aliquot from every patient sample is to allow for unusually large variances from normally expected tests results that might occur, for instance, as a result of unrecognized operator error or reagent or analyzer failure.

It should be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention.

Accordingly, while the present invention has been described herein in detail in relation to specific embodiments, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

What is claimed is:

1. A system for directly re-supplying a sample aliquot contained in an aliquot array to an analyzer for testing without operator intervention, wherein the re-supplying system comprises:
    an analyzer having a number of aliquot array sampling tracks;
    at least one aliquot array disposed within one of said aliquot array sampling tracks;
    an aliquoting probe proximate said sampling tracks and comprising aspiration means for aspirating aliquot sample portions from an original patient sample container and dispensing at least one aliquot sample portion into said at least one aliquot array;
    an aliquot array handling unit disposed proximate a first end of said sampling tracks and comprising at least one aliquot array inventory shaft sized for containing aliquot arrays therein;
    at least one aliquot array storage rack disposed proximate a second end of said sampling tracks and comprising a number of aliquot array storage shafts, each shaft having a spaced apart vertical array of a plurality of slots, each slot sized to support one aliquot array;
    drive motors positioned proximate said sampling tracks for removing the aliquot array from said at least one aliquot array inventory shaft, moving the aliquot array along one of said sampling tracks, and placing the aliquot array into one of said slots in the aliquot array storage rack;
    an environmentally controlled chamber disposed proximate said aliquot array sampling tracks and comprising a rotatable carousel therein, the carousel adapted for storing said aliquot array storage rack; and
    elevation means disposed above said chamber and having a motor for placing said aliquot array storage rack into said carousel and removing said aliquot array storage rack from said carousel.

2. The system of claim 1 further comprising a sampling probe for aspirating test sample portions from the aliquot sample portion and dispensing said test sample portions for testing.

3. The system of claim 1 further comprising indicia on the original patient sample container that dictate the period of time that a sample aliquot portion is to be retained in the storage chamber after a first sample aliquot is aspirated.

4. The system of claim 1 further comprising indicia on the original patient sample container to indicate the tests to be performed upon a patient's sample and the period of time for storing said aliquot sample portion within said storage chamber.

5. The system of claim 1 wherein the elevation means for removing the aliquot array storage rack from the rotatable carousel comprises a latch arm attached to a vertical drive shaft and having C-shaped hooks depending therefrom.

6. The system of claim 5 wherein the aliquot array storage rack further comprises knobs slideably engaged by the C-shaped hooks of the latch arm while stored in said rotatable carousel.

7. The system of claim 1 wherein the number of aliquot array storage racks is the same as the number of aliquot array test sampling tracks, and the aliquot array storage racks and aliquot array test sampling tracks are horizontally spaced in alignment with one another.

8. The system of claim 1 wherein the analyzer is controlled by a computer programmed to confirm that the aliquot sample portion has been retained within said chamber for less than an assay-specific length of time prior to aspirating test sample portions.

9. The system of claim 1 wherein the analyzer is controlled by a computer programmed to not re-supply sample aliquots if the aliquot sample portion has been retained within the environmentally controlled chamber for greater than an assay-specific length of time.

* * * * *